(12) United States Patent
Bierbaum et al.

(10) Patent No.: US 7,685,866 B2
(45) Date of Patent: Mar. 30, 2010

(54) LEAKAGE CHECKING AND CALIBRATING OF A LIQUID DELIVERY SYSTEM

(75) Inventors: Alexander Bierbaum, Karlsruhe, CO (US); Hans-Georg Weissgerber, Straubenhardt, CO (US); Konstantin Choikhet, Karlsruhe, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 806 days.

(21) Appl. No.: 11/221,158

(22) Filed: Sep. 7, 2005

(65) Prior Publication Data

US 2006/0174697 A1    Aug. 10, 2006

(30) Foreign Application Priority Data

Feb. 4, 2005   (EP) ................... 05100764

(51) Int. Cl.
*G01M 3/08*    (2006.01)

(52) U.S. Cl. .............................. 73/46; 73/40
(58) Field of Classification Search ........... 73/46
See application file for complete search history.

(56) References Cited

U.S. PATENT DOCUMENTS 4,681,513 A    7/1987    Saito et al.

FOREIGN PATENT DOCUMENTS

| EP | 0309596 | 4/1989 |
|---|---|---|
| EP | 0471930 | 2/1992 |
| WO | WO 03/079000 | 9/2003 |
| WO | WO 2005/050190 | 6/2005 |

*Primary Examiner*—Daniel S Larkin
(74) *Attorney, Agent, or Firm*—Marc Bobys (57) ABSTRACT

A liquid delivery system having at least one channel, at least one valve within that channel, at least one flow sensing device within that channel, and a pressure source downstream of the valve capable for generating variable pressures.

3 Claims, 4 Drawing Sheets

LEAKAGE CHECKING AND CALIBRATING OF A LIQUID DELIVERY SYSTEM

BACKGROUND ART

1. Field of the Invention

The present invention relates generally to methods for executing and controlling liquid delivery processes.

2. Discussion of the Background Art

Such systems generally serve for any biological, chemical, and/or physical synthesis analysis or dosage process. The system performance and the quality of the performance of the synthesis analysis or dosage processes, depend, along with other influential factors, on the system pressure and the flow rate of a liquid delivery system. Very common are, for example, High Performance Liquid Chromatography systems. HPLC is a form of chromatography used to separate compounds that are dissolved in liquid. For this purpose, the liquid can be delivered in a more or less constant flow, for example, by a binary pump as disclosed in the EP0309596A1. Such a binary pump can generate an uninterrupted and constant flow of liquid. Besides this, it is possible to generate a solvent gradient.

Sensors, for example pressure sensors and flow rate sensors, can be employed for measuring the process values during liquid delivery. Known are flow rate sensors measuring a pressure drop across a fluidic restriction, for example as disclosed in the paper: "A High-Precision Piezoresistive Flow Sensor for Microdosing Applications" of Marc Boillat, Bart van der Schoot, and Bastien Droz, Seyonic S A, published on the Internet under http://www.sensorsmag.com/articles/0900/129/main.shtml.

Other flow rate sensors comprise a heating element and measure a temperature difference within the flowing fluid upstream and downstream of the heating element. Such sensors are disclosed for example in the paper: "A precision thermal mass flow sensor for small liquid flows" of Ir. H. J. Boe and Ing. W. Derks; published on the Internet under http://www.bronkhorst.com/pdf/thermal.pdf, and are delivered, for example, by the company Sensirion AG, Eggbuehlstrasse 14, CH-8052 Zurich, Switzerland, http://www.sensirion.com.

SUMMARY OF THE INVENTION

According to embodiments of the present invention, a liquid delivery system having at least one channel, at least one valve within that channel, at least one flow sensing device within that channel, and a pressure source downstream of the valve capable of generating variable pressures is suggested. Advantageously, such a liquid delivery system can be used for leakage checking and calibrating itself. The liquid delivery system can be, for example, a high pressure solvent delivery system, such as a HPLC pump.

Embodiments may comprise one or more of the following. The channel comprises two parts, a first and a second channel. The valve and the pressure source are adapted for increasing the pressure within the second channel up to a significant higher pressure than in the first channel and for preventing the opposite. For this purpose, the valve can be realized as a flow check valve, on-off valve, and/or flow control valve or any other suitable valve. The parts of the channel can behave like chambers.

At its beginning respectively upstream of the valve the first channel comprises the flow source. The channel can conduct a fluid, for example a liquid, in particular a flow of liquid delivered by the flow source. The flow source is capable of delivering liquid. The flow sensing device can be realized as a flow sensor or rather flow rate sensor. Such flow rate sensors or rather flow sensing devices normally have a non-linear characteristic and can be used for maintaining the desired flow rate within the channel. Besides this, the non-linear characteristic differs for different solvents. In other words, the response of the available flow rate sensors is generally non-linear and different for each type of used solvents. The signal characteristics of such mass flow sensors depend strongly on the physical properties of the solvent, for example, density, viscosity, thermal conductivity, and specific heat. This problem arises in particular for very high system pressures and very low flow rates, for example pressures higher than 100 bar and flow rates as low as 1 to 10 micro liters per minute.

Downstream of the flow source at least one flow rate sensor or rather flow sensor is arranged and downstream of the flow rate sensor at least one valve. The valve can be realized as a flow check valve or as any other valve or functional element enabling a similar functionality as a flow check valve. Possibly, the flow rate sensor can be arranged downstream of the flow check valve. Downstream the first channel is coupled behind the flow check valve to the second channel. The flow check valve prevents any liquid from streaming back to the first channel from the second channel. At its end, the second channel comprises a flow resistance, in particular a restriction. In other embodiments, no additional parts are needed because the restriction results from the system-inherent flow resistance within the second channel.

Embodiments may comprise one or more of the following. The flow resistance can be coupled to a drain. In embodiments, the flow restriction can have an infinite resistance; realized, for example, as stop plug. The pressure source can pressurize the second channel against the flow check valve and the flow resistance. For this purpose, the pressure source is coupled to the second channel upstream of the flow resistance and downstream of the flow check valve. The pressure source can comprise any liquid delivery system in combination with a pressure sensor and a controller connected in a feedback loop.

Embodiments may comprise one or more of the following. The flow source and the pressure source are adapted for producing different flows and pressures of a liquid within the channel of the liquid delivery system. While producing different pressures and flows, the flow sensing device produces readings. Advantageously, the pressures and flows can be produced in a manner that the readings can be used for leakage checking the system and/or for calibrating the flow sensing device.

Advantageously, a flow source is adjustable to at least one constant flow rate set point. Besides this, the pressure source is adapted for pressurizing the second channel to values of at least two different pressure set points. Advantageously, the flow rate sensor is adapted for measuring the flow rate within the first channel while setting the flow source and/or the pressure source to different set points. Advantageously, this configuration and setting can be used for executing a system leakage check. Leakage checking of a hydraulic system or part of it is usually performed by blocking all outlets and pressurizing the system to a certain pressure. If the pressure is decreasing after the pressure source is deactivated, the system might be considered leaking. Such blocking plugs are not required in said configuration.

Normally, leakage flows are dependent on the system pressure. As a premise for the leakage check, the flow source is adjusted to a constant flow rate. This constant flow rate can be measured by the flow rate sensor at two different system pressures. Due to said dependency, the comparison of the measurement response of the flow rate sensor at the two different system pressures, allows a statement about system tightness. Besides this, internal leakages, for example of the flow check valve not closing properly, can be detected by this method. This leakage check can be run in a system set up for standard liquid chromatography operation. No manual manipulation of the system configuration is required.

Advantageously, the absolute value of the response value of the flow rate sensors at the two different pressures is not relevant. For detecting the system tightness, just a difference of a first signal of the flow rate sensor generated at a first lower system pressure and a second signal of the flow rate sensor generated at a second higher system pressure is enough. Especially advantageously, any difference differing from zero indicates that the system is not tight.

It can be seen, that this leakage check can be done with any non-calibrated flow rate sensor within the delivery cannel. Consequently, the leakage check can be executed as a qualitative leakage check. The absolute leakage flows do not have to be determined. Generally, for measurement of absolute leakage flows, a calibrated flow rate sensor is often required. Advantageously, a calibration of a flow rate sensor can be performed in the same system without uninstalling the flow rate sensor, if the leakage check showed a sufficiently leakage-free system. For this purpose, the flow source can be run at different known flow rate set points under the premise, that the flow delivered by the flow source through the flow rate sensor has a correct value, because there are no flow losses in a leak-free system. At these known flow rates, the response value of the flow rate sensor can be detected. With this, the characteristic of the flow rate sensor can be logged.

Embodiments may comprise one or more of the following. Advantageously, the system can be leakage-checked and after that calibrated without uninstalling any parts. The two tests can be executed before running a new analysis engaging another solvent. This can be required since the flow rate sensor typically has different characteristic curves for different solvents.

Embodiments may comprise one or more of the following. Advantageously, the flow source comprises a first piston or rather head of a two-piston pump. The pressure source can comprise a second downstream piston or rather head of the two-piston pump. In this setup, the flow check valve is the outlet valve of the two-piston pump. Such a two-piston pump is disclosed in the EP0309596A1, which is incorporated herein by reference. In particular, the figures and the according description showing the pump are included herewith in this application. The flow rate sensor is inserted between the two heads of the two-piston pump, downstream of the first head and upstream of the second head. The second piston or head can serve as a pressure controlled flow source while the first piston or head of the two-piston pump delivers a stabilized flow of fluid, for example liquid.

Advantageously, any system leakage of the first piston and/or of the outlet valve of the binary pump can be detected in this configuration by executing the leakage check as described above.

Embodiments can comprise one or more of the following. Advantageously, the system can comprise a plurality of parallel-connected first channels. The first channels each are coupled to the second channel. Advantageously, the leakage check and calibration can be executed with these parallel-connected first channels as well. Especially advantageously, the leakage check can be executed in parallel for each first channel. Such systems with a plurality of parallel-connected first channels, in particular two first channels, can be used for generating a solvent gradient. Therefore, the different channels deliver different time-dependent flow rates of different liquids to the second channel.

Embodiments can comprise one or more of the following: The system comprises a pressure sensor for detecting the system pressure; the pressure sensor is arranged downstream of the valve for measuring the pressure in the second channel; the flow sensing device is realized as a flow rate sensor; the flow rate sensor is located downstream of the valve for measuring the flow of the liquid within the second channel; alternatively, the flow rate sensor is located upstream of the valve for measuring the flow of the liquid within the first channel; the flow rate sensor is located downstream of the flow source for measuring the flow of the liquid within the channel being delivered by the flow source; the valve is realized as a flow check valve for controlling the direction of the flow within the channel; the channel is connected to a hydraulic flow resistance for inducing a pressure within the channel; the channel comprises at least one first channel and at least one second channel; the first channel is coupled upstream of the valve; the second channel is coupled downstream of the valve; the second channel comprises the hydraulic flow resistance for inducing a pressure between the valve and the flow resistance; the resistance comprises a restriction; the resistance comprises a valve; the resistance comprises an adjustable valve; the first channel comprises the flow source for transporting liquid through the first channel; the pressure source is coupled upstream of the resistance to the second channel for inducing a pressure within the channel, in particular within second channel between the valve and the flow resistance; the pressure source is coupled downstream of the valve to the second channel for inducing said pressure; the flow source is adjustable to at least one constant flow rate set point for producing a constant known flow within the channel; the pressure source is adapted for pressurizing the first channel and/or the second channel to at least one pressure value producing a constant known pressure within the channel; the flow rate sensor is adapted for measuring the flow rate within the first channel; the flow rate sensor is adapted for measuring the flow rate within the channel, in particular within the first channel, while setting the flow source and/or the pressure source to different set points, preferably for checking the system for leakage; the flow rate sensor is adapted for measuring the flow rate within the channel, in particular within the first channel, while setting the flow source to different set points, preferably for calibrating the flow rate sensor.

Besides this, embodiments of the invention relate to methods for leakage checking and calibrating a liquid delivery system.

More precisely to a method of leakage checking of a valve of a liquid delivery system:

Firstly, the second channel of the liquid delivery system is pressurized. Subsequently, the flow rate within the channel of the liquid delivery system is measured with a flow rate sensor. Finally, the measured values for at least two different pressure values are compared to each other or to the known zero point value of the flow rate sensor. Advantageously, the readings of the flow rate sensor at the different pressures can be compared or rather interpreted for detecting any crossing over leakage of the valve.

Besides this, embodiments of the invention relate to a method of leakage checking of a channel of a liquid delivery system upstream of a valve:

Firstly, the second channel of the liquid delivery system is pressurized to a first pressure p1. Subsequently, a first flow q1 is produced within the first channel of the liquid delivery system with a flow source. After that, the flow rate is measured within the first channel with a flow rate sensor. Subsequently, the second channel is pressurized to a second pressure p2. Finally, the flow rate is measured within the first channel with a flow rate sensor again. Advantageously, the readings of the flow rate sensor can be interpreted for leakage checking the system.

Embodiments may comprise one or more of the following. The two methods as described above can be combined to one method and/or supplemented by one or more of the following before, during, or after executing the single features of each method:

The flow source can be set to zero flow for depressurizing the channel respectively the first channel. The flow rate within the channel of the liquid delivery system can be measured with the flow rate sensor, at least once while executing pressurization. Besides this, readings of multiple measurements can be used averaged or filtered or processed in any other way. The flow rate can be measured within the first channel with the flow rate sensor at least once at the same flow rate setting of the flow source.

The measured flow rate values can be compared before and after the valve, in particular the flow check valve opens accordingly. The flow source produces an increasing pressure within the first channel until the flow check valve opens accordingly.

Embodiments of the invention further relate to a method of calibrating a flow rate sensor in a liquid delivery system comprising:

Firstly, a plurality of flows q1 to qn is produced within the first channel of the liquid delivery system by means of the flow source. Additionally, the flow rate can be measured with the flow rate sensor. The flow rate can be measured within the channel, in particular within the first channel, with the flow rate sensor at least once while each flow q1 to qn is set by the flow source. Advantageously, the readings of the flow rate sensor can be interpreted for calibrating the flow rate sensor.

Embodiments may comprise one or more of the following. Advantageously, the system can be leakage checked before executing the method respectively calibrating the flow rate sensor. The second channel can be maintained at a third pressure p3 by the pressure source, in particular to a pressure p3 of zero, preferably the pressure source can be switched off before producing the plurality of flows q1 to qn are produced and the flow rates are measured. Advantageously, a method of leakage checking as described above can be combined with the method of calibrating the flow rate sensor. The system can be leakage checked before executing the calibration.

Embodiments may comprise one or more of the following. The method comprises pressurizing the second channel of the liquid delivery system to a first pressure p1, for example 10 bar, and producing a first flow q1, for example of 10 micro liter per minute, within a first channel of the liquid delivery system. Subsequently, the second channel is pressurized to a second pressure p2, for example 150 bar. Possibly, the liquid delivery system is adapted for delivering liquid under significant higher pressures than p2. The pressure p2 is just an exemplary value possibly usable for testing the system. Finally, the flow rate within the first channel can be measured with a flow rate sensor at least once while executing each of the features as described above.

Embodiments may comprise one or more of the following. This method can be used for detecting leakages in the system by combining measurements of pressures, flows as metered by flow sources and flow values as measured by the flow rate sensors.

Advantageously, after passing the leakage test, the flow rate sensor of the system can be calibrated. For this, the flow source of the system can be set to a plurality of different flow rates while measuring the response values of the flow rate sensor.

Finally, embodiments relate to a liquid delivery system comprising a flow rate sensor. The liquid delivery system is adapted for executing at least one of the following methods: The method for leakage checking and calibrating a liquid delivery system as described above, the method of leakage checking a channel of a liquid delivery system upstream of a valve as described above, and the method of calibrating a flow rate sensor in a liquid delivery system as described above. Advantageously, the liquid delivery system, for example a solvent delivery system for a high performance liquid chromatography system, can be checked automatically for any leaks, for example before starting delivering. Any side effects caused by any leak affecting the results of the HPLC can be reduced to a minimum. The check can be regarded as automated as the user will not need to plug hydraulic pathways manually or use valves to check the system tightness, instead the system may be tested in the same configuration as for solvent delivery.

Embodiments of the invention can be partly or entirely embodied or supported by one or more suitable software programs, which can be stored on or otherwise provided by any kind of data carrier, and which might be executed in or by any suitable data processing unit. Software programs or routines are preferably applied for executing at least one of the following methods: The method for leakage checking and calibrating a liquid delivery system as described above, the method of leakage checking a channel of a liquid delivery system upstream of a valve as described above, and the method of calibrating a flow rate sensor in a liquid delivery system as described above. Consequently, for executing the leakage check, the flow rate sensor calibration, and besides this for controlling the set points of the system while running said check and/or calibration.

BRIEF DESCRIPTION OF THE DRAWINGS

Other objects and many of the attendant advantages of embodiments of the present invention will be readily appreciated and become better understood by reference to the following more detailed description of preferred embodiments in connection with the accompanied drawings. Features that are substantially or functionally equal or similar will be referred to with the same reference sign(s).

DETAILED DESCRIPTION OF THE PREFERRED EMBODIMENT

Figure 1:
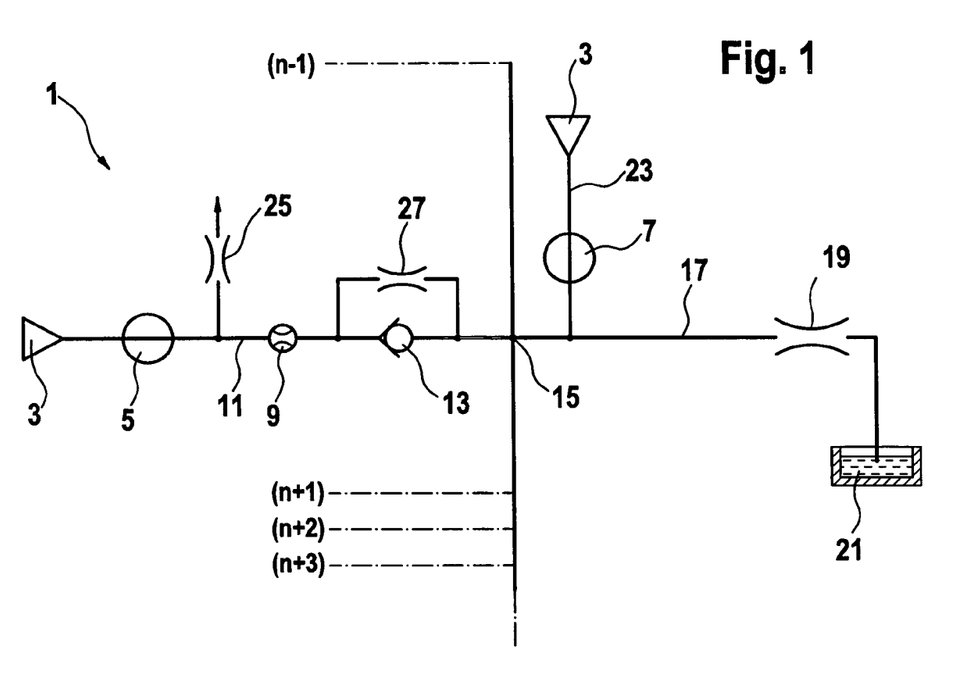
FIG. 1 shows a generic hydraulic set-up of a liquid delivery system adapted for executing an automated leakage check and/or calibration.

FIG. 1 shows a generic hydraulic set-up of a liquid delivery system 1. In analytical work, generally flow rates of about 100 µl/min to 1 ml/min, for example 10 µl/min, are employed. The liquid delivery system comprises a reservoir 3 for supplying the system with a liquid. The reservoir 3 can supply the system without pressure or at a low-pressure level. The reservoir 3 is coupled downstream to a flow source 5 and to a pressure source 7. For this purpose, the system can comprise just one reservoir 3 or two different reservoirs 3 comprising the same or different liquids. The flow source 5 is coupled downstream to a flow rate sensor 9 adapted for measuring the flow rate within a liquid first channel 11 of the liquid delivery system 1.

Besides this, the first channel 11 comprises a flow check valve 13 downstream of the flow rate sensor 9. The first channel 11 is coupled downstream at a coupling point 15 to a second channel 17 of the liquid delivery system 1. The second channel 17 of the liquid delivery system 1 is coupled downstream to a restriction 19, for example a restriction. The restriction 19 is coupled downstream to a drain 21. A branch 23 coupled to the second channel 17 comprises the pressure source coupled to the reservoir 3 or to a separate reservoir. In embodiments, the pressure source can pressurize the second channel 17 to arbitrary constant pressures. The pressure source 7 can pressurize the second channel 17 downstream of the flow check valve 13 and upstream of the restriction 19.

In embodiments, the restriction 19 can be realized as a liquid tight plug-up. In other embodiments, the restriction 19 results from the system-inherent flow resistance within its second channel 17. In other words, the pressure source 7 is adapted for generating a constant pressure behind the flow check valve 13. The flow check valve 13 in a hydraulic set-up as shown in FIG. 1 behaves as follows: In a first setting, with a lower pressure in the first channel 11 as in the second channel 17, the flow check valve 13 is closed. In a second setting, with a higher pressure in the first channel as in the second channel 17, the flow check valve 13 opens. Because of the pressure-controlled condition within the second channel 17 of the liquid delivery system 1, the difference between the pressures in the first channel 11 and the second channel 17 adjusts itself up to a value according to the pressure drop of the flow check valve 13 in the opened state. In this opened state of the flow check valve, different flow rates can be generated by the flow source whereas the pressure source maintains a constant pressure in the system by adjusting the flow generated by the said pressure source.

This system operation mode can be engaged for detecting a first leakage 25 of the first channel 11 and a second crossing over leakage of the flow check valve as follows:

Firstly, the first channel 11 can be depressurized. After that, the second channel 17 of the liquid delivery system 1 can be pressurized up to a first pressure p1 by the pressure source 7. After that, the flow source 5 can be adjusted to a constant flow rate within the first channel 11. This causes a linearly increasing pressure within the first channel 11 due to the compressibility of the liquid—under the premise of a system 1 without any elasticity—within the first channel up to a value of the constant pressure generated within the second channel 17 by the pressure source plus the value of the pressure drop of the flow check valve 13. The flow rate sensor 9 is positioned relatively close to the flow check valve 13. Because of this, the responded value of the flow rate sensor 9 in this phase should be approximately zero.

After opening of the flow check valve 13 caused by the increasing pressure within the first channel 11, the responded value of the flow rate sensor should correspond to the flow rate produced by the flow source 5. With an uncalibrated flow rate sensor 9 the flow rate value cannot be determined. Because of this and because of the non-linear characteristic curve of the flow rate sensor 9, a statement about the system tightness cannot be made by executing this alone. To be able to make a statement about the system tightness, the features as described above or rather the measurement of the flow rate can be repeated at another pressure level within the second channel 17 generated by the pressure source 7 of the liquid delivery system 1.

The system leakages 25 and 27 usually depend on the pressure at the leak location. This causes a difference of the leakage flow rates at different system pressures, consequently detectable with the flow rate sensor 9. This difference of leakage flows is also detectable with an uncalibrated flow rate sensor 9 as difference in sensor readings at different pressures. Advantageously, the system tightness can be detected with an uncalibrated flow rate sensor 9 in a qualitative manner.

Advantageously, the flow check valve 13 and the flow rate sensor 9 can be positioned to each other as close as possible for minimizing any side effects, for example caused by any flow resulting of the compressibility of the liquid within the channel of the liquid delivery system 1.

In embodiments, the liquid delivery system 1 comprises one or more first channel(s) 11. Such first channels to are indicated in FIG. 1 by dash dotted lines. The parallel-connected first channels n each are coupled to the second channel 17 at the coupling point 15. Advantageously, leakage checks within the parallel first channels n can be run in parallel.

Figure 2:
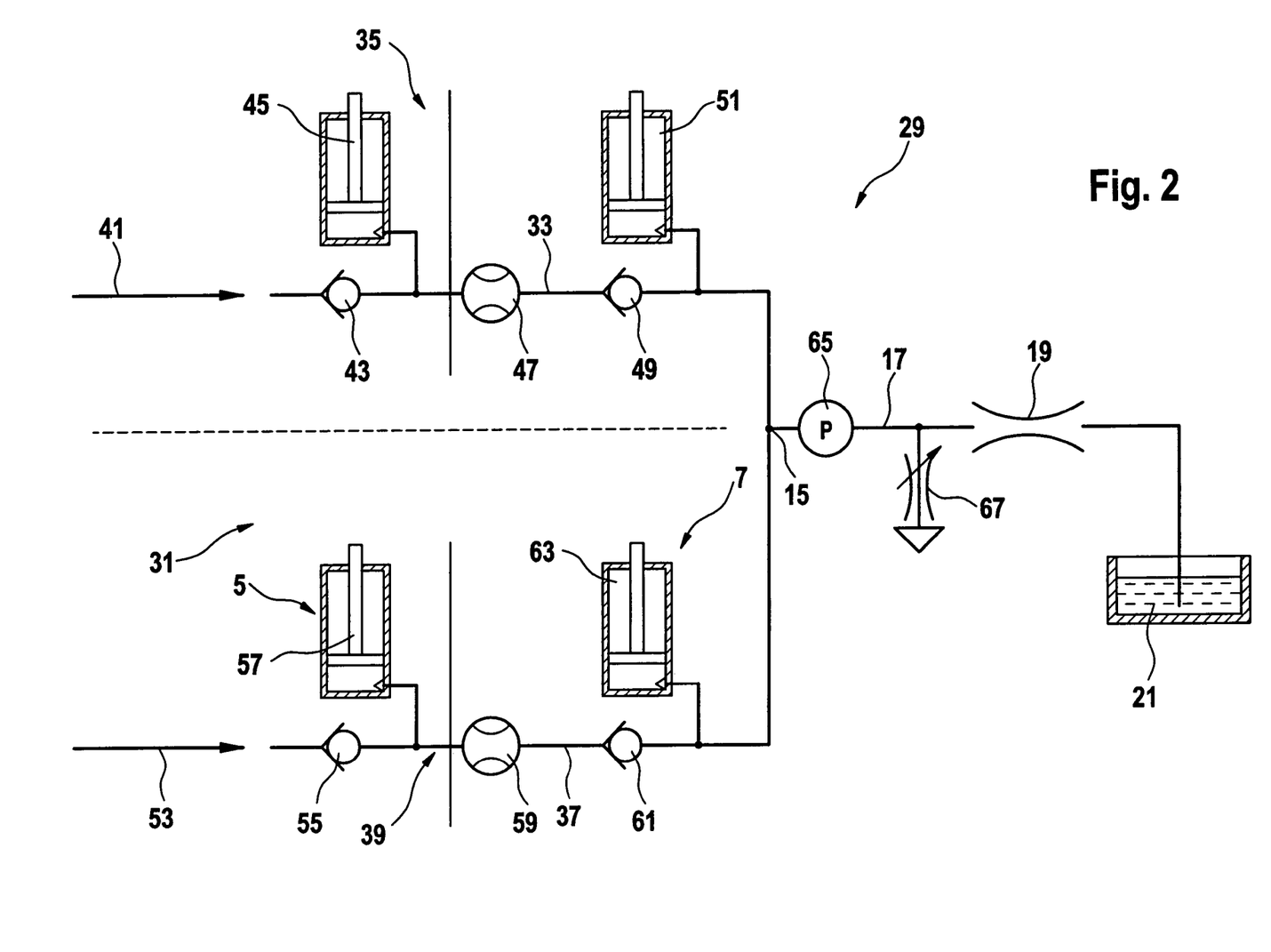
FIG. 2 shows a binary two piston pump configuration with two parallel-connected two piston or binary pumps adapted for executing an automatic leakage check and/or calibration.

FIG. 2 shows another liquid delivery system 29 comprising a pump 31. The pump 31 comprises a first liquid delivery channel 33 with a first two-piston pump 35 and a second liquid delivery channel 37 comprising a second two-piston pump 39. The delivery channels 33 and 37 of the pump 31 correspond to the first channel(s) as described above. The liquid delivery channels 33 and 37 are coupled downstream to the second channel 17 at the coupling point 15.

The first two-piston pump 35 is coupled to a not shown reservoir, as symbolized with an arrow 41 and comprises at its intake an inlet valve 43, downstream of the inlet valve 43 a first piston 45, downstream of the first piston 45 a flow rate sensor 47, downstream of the flow rate sensor 47 an outlet valve 49, and finally downstream of the outlet valve 49 a second piston 51. Accordingly, the second two-piston pump 39 comprises at its intake, symbolized by an arrow 53 an inlet valve 55, a first piston 57, a flow rate sensor 59, an outlet valve 61 and finally a second piston 63. In embodiments, the second channel 17 of the liquid delivery system 29 can comprise a pressure sensor 65. Besides this, in embodiments the second channel 17 of the liquid delivery system 29 can be coupled to a purge valve 67 for purging the system. In embodiments, the restriction 19 of the system cannel 17 of the liquid delivery system 29 is removable, consequently not part of the liquid delivery system 29.

The restriction 19 can be added to the liquid delivery system for executing a leakage check and/or a flow rate sensor calibration as described above. For leakage checking the first liquid delivery channel 33, the first piston 45 of the first two-piston pump 35 can serve as the flow source as described above and the second delivery channel 37 of the second two-piston pump 39 can serve as a pressure source as described above. In embodiments, just the second piston 51 of the first two-piston pump 35 can serve as the pressure source for leakage checking the first liquid delivery channel 33 of the first two-piston pump 35.

In this case, the test has to be timed carefully, because the volume of one stroke of the second piston 51 of the first two-piston pump 35 is limited. If the restriction 19 is not infinite, for example with a blocking plug or an electromagnetic valve, the second piston 51 of the first two-piston pump 35 will constantly need to deliver liquid while keeping the pressure and thus will need to return when displaced all its volume. The leakage check can often cover the most important leak origins, which are "cross leakage" over the outlet valves 49 and/or 61 of the pumps 35 and/or 39 and leaks upstream the outlet valve, for example of the pistons 45 and/or 57. Leaks in the pistons 51 and/or 63 are rare.

Figure 3:
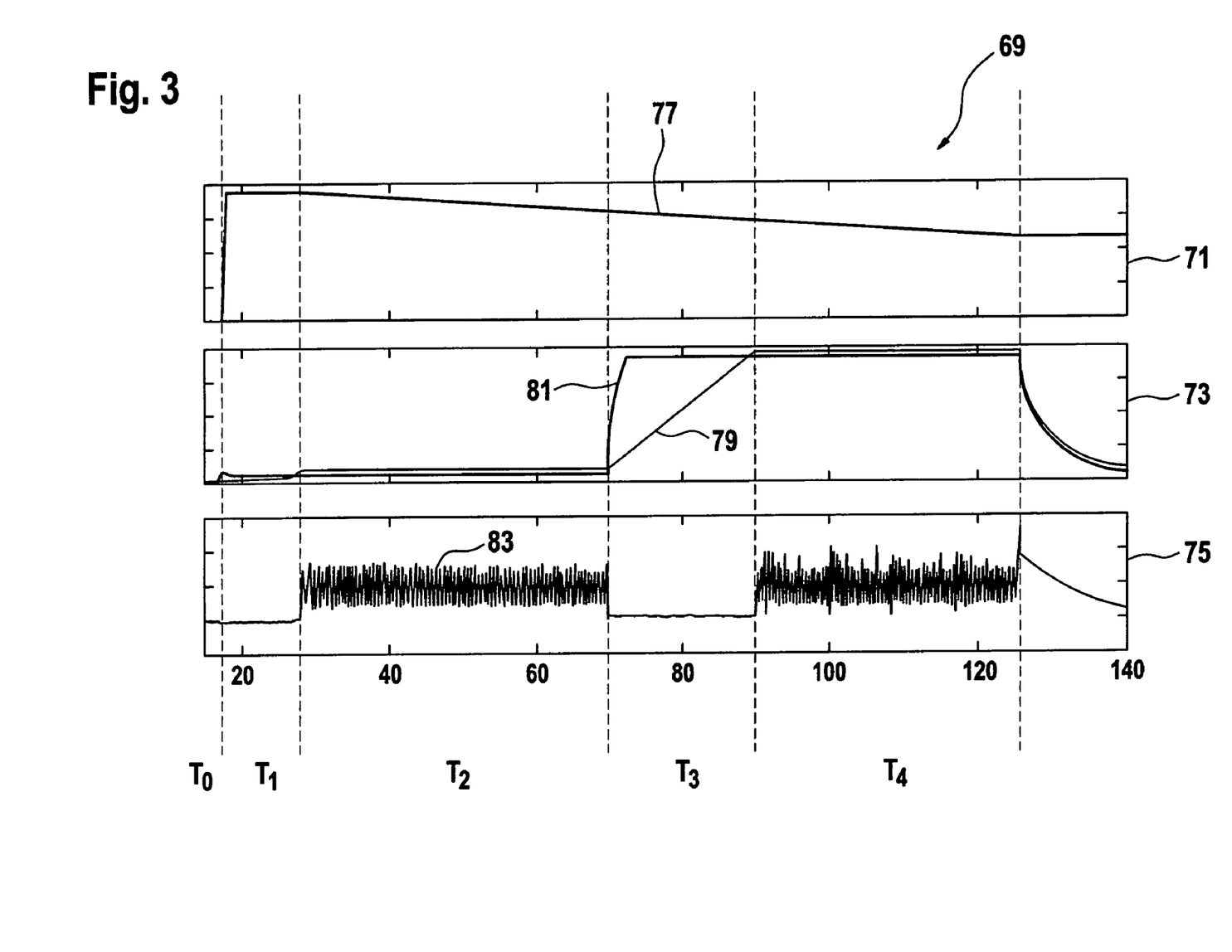
FIG. 3 shows a timing diagram of an automated leakage check showing the variation of time of different values of the configuration of FIG. 2.

FIG. 3 shows a timing diagram of an automated leakage check showing the variation of time of different values of the configuration as described in FIG. 2.

In this embodiment, the X-axis of the timing diagram 69 shows the time in seconds from zero seconds up to 140 seconds. The timing diagram 69 shows three different single diagrams, a first diagram 71, a second diagram 73, and a third diagram 75.

The first diagram 71 shows a first plot 77 of the actual position of the first piston 57 of the second two-piston pump 39. The Y-axis of the first diagram 71 represents the actual position of a stroke of the piston 57. A value on the x-axis of the first diagram 71 of the first plot 77 represents the position of the first piston 57 at the end of a complete stroke when all the volume of the first piston 57 is displaced.

The second diagram shows two plots 79 and 81 of two pressures within the liquid delivery system 29. A second plot 79 shows the pressure within the second liquid delivery channel 37 of the second two-piston pump 39. For measuring this pressure, the second liquid delivery channel 37 of the second two-piston pump 39 can comprise an additional, not shown pressure sensor. A third plot 81 shows the pressure captured by the pressure sensor 65 within the second channel 17 of the liquid delivery system 29.

The Y-axis of the third diagram 75 represents the response value of the flow rate sensor 59 of the second liquid delivery channel 37 of the second two-piston pump 39. The signal generated by the flow rate sensor 59, as represented by a fourth plot 83 of the third diagram 35 of the timing diagram 69, is noisy but can be filtered if necessary.

The leakage test as represented by the timing diagram 69 as shown in FIG. 3 is executed in five time phases, represented by the capital letters T0, T1, T2, T3, and T4. In an initial phase T0, the second liquid delivery channel 37 of the second two-piston pump 39 and the second channel 17 are depressurized, which can be seen in the plots 79 and 81 of the second diagram 73.

After that, the first phase T1 starts by generating a constant flow rate by the first piston 57 of the second two-piston pump 39. This can be done by moving the piston 57 with a constant velocity, as represented by a constant gradient of the first plot 77 in the first diagram 71. Concurrently, the pressure within the second channel 17 has to be adjusted to a first constant pressure p1. This can be done by employing one of the second pistons 51 or 63 of the two-piston pumps 35 and 39 as pressure source.

The transient up to the first constant pressure p1 is shown in the plot 81 of the second diagram 73. Advantageously, the pressure sensor 65 and a not shown pressure controller can be used for this purpose. In this first phase T1 the outlet valve 61 of the second two-piston pump, which is realized as a check valve, is closed. During the phase T1 the pressure within the second liquid delivery channel 37 increases up to a value of the opening pressure of the outlet valve 61. The liquid delivery channel 37 behaves like a chamber in this phase T1. For a tight system readings of the flow rate sensor 59 correspond to zero flow rate. Consequently, the liquid delivery channel 37 upstream of the outlet valve 61 behaves like a pressure-tight chamber in this phase T1 if no leakage occurs.

In the second phase T2, the outlet valve 61 of the second two-piston pump 39 is opened. The readings of the flow rate sensor 59, as represented by the fourth plot 83 of the third diagram 75, increase to a second value. The pressure within the second channel 17 is still the same due to pressure controlling.

The pressure within the second liquid delivery channel 37 as represented by the second plot 79 of the second diagram 73, is equal to the value of the first constant pressure p1 within the second channel 17 plus the pressure drop of the outlet valve 61 of the second two-piston pump 39.

In a third phase T3, the pressure within the second channel 17 of the liquid delivery system 29 is increased approximately in a jump to a second pressure p2. The transient up to the second constant pressure p2 is shown in the plot 81 of the second diagram 73. This causes an approximately linear pressure increase within the second liquid delivery channel 37 of the second two-piston pump 39, which can be seen in the second plot 79 of the second diagram 73. Induced by the constant flow delivered by the first piston 57, the pressure increases again up to a level of the pressure p2 plus the pressure drop of the outlet valve 61. During this phase T3, the flow indicated by the flow rate sensor 59 drops to the same value as in the first phase T1. This indicates that the system is tight. Consequently, the liquid delivery channel 37 upstream of the outlet valve 61 behaves like a pressure-tight chamber in this phase T3 if no leakage occurs. Other values differing from the value of the first phase would indicate a system leakage.

The flow rate sensor 59 is arranged close to the outlet valve 61. Therefore, any differences of the output values of T1 and T3 of the flow rate sensor would indicate a crossing over leakage of the outlet valve 61.

In a fourth phase T4 of the leakage test as plotted in FIG. 3, the outlet valve 61 opens again. This results in an increased output value of the flow rate sensor 59. The leakage test as represented in FIG. 3 shows a 100% tight system. This means that the response values of the flow rate sensor 59 in phases T1 and T3 and in phases T2 and T4 are identical. The phases T2 and T4 have to be executed at least as long as the response values of the flow rate sensor 59 need to reach a steady state and to provide sufficient data base for averaging.

Figure 4:
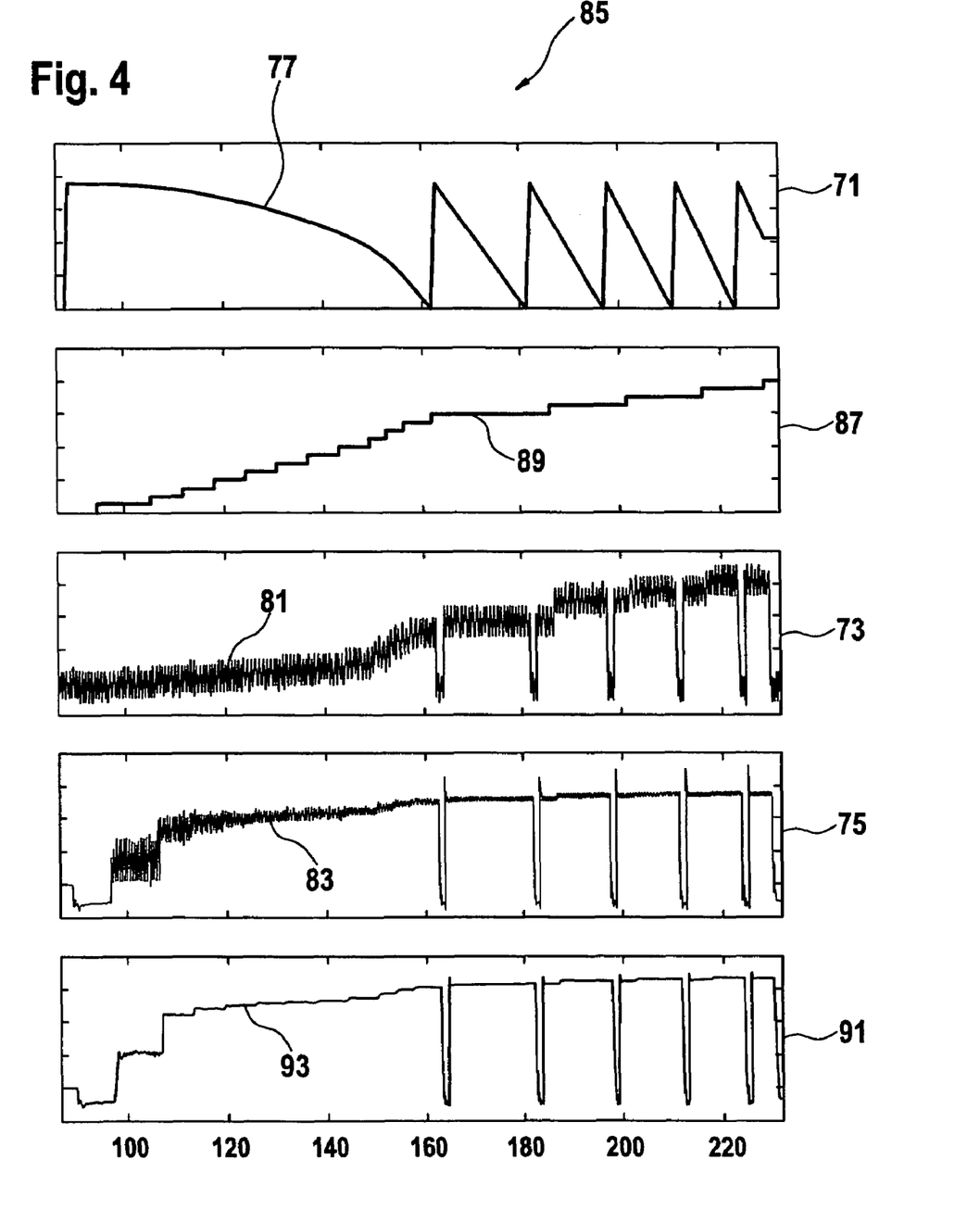
FIG. 4 shows another timing diagram of a calibration of a flow rate sensor showing the variation of time of different values of the configuration of FIG. 2.

FIG. 4 shows another timing diagram of a calibration of a flow rate sensor 59 showing the variation of time of different values of the configuration of the liquid delivery system 29 as shown in FIG. 2.

Additionally, the timing diagram 85 shows a fourth diagram 87 showing a fifth plot, representing a flow rate index of the flow source 5 or rather of the first piston 57 of the second two piston-pump 39 of the second liquid delivery system 29. Besides this, the timing diagram 85 shows a fifth diagram 91 showing a sixth plot 93 of the filtered output value of the flow rate sensor 59

The timing diagram 85 as shown in FIG. 4 represents a complete plot of 16 increasing flow rate values of a flow rate sensor calibration for the flow rate sensor 59 of the liquid delivery system 29 as shown in FIG. 2. For this purpose, the flow rate delivered by the piston 57 is increased according to the flow rate index 89, first in one stroke with increasing velocity and than in different strokes of the piston 57 especially for the higher flow rates. This is because the flow rate sensor signal needs more time at higher flow rates to become stable. In embodiments, the calibration can be run with just one stroke. The gradient of the plot 77 represents the different velocities and accordingly the different flow rates generated by the piston 57. For obtaining the characteristic curve of the flow rate sensor 59, the according output values of the flow rate sensor 59 are plotted in the diagram 75 or rather in the diagram 91. In a multi-channel system, for example in a system according to FIG. 2, this procedure can be repeated until all flow rate sensors 47 and 59 are calibrated.

Advantageously, the flow rate sensors 47 and 59 in parallel liquid delivery channels 33 and 37 can be calibrated in parallel. The number and range of the different calibration flow rates both can be defined according to the sensitivity of the expected flow rate sensor characteristics of the flow rate sensor 9.

Thus, this calibration run takes measurements at a number of, for instance 16 flow rates including zero flow. Consequently, this calibration run needs several piston strokes especially for the higher flow rates. This is because the flow rate sensor needs significant flow-through volume at high flow rates before the readings are reliable.

Advantageously, obtaining the absolute values as given in the calibration of the flow rate sensor can be done after the system has been checked in a qualitative leakage check for any leakages as described above.

In the following, a method of leakage checking and calibrating a liquid delivery system is described by referring to the Figures above:

At first, the second channel 17 of the liquid delivery system I is pressurized downstream of the valve 13 to a first pressure p1. The second channel 17 downstream of the valve 13 behaves like a pressure-tight chamber coupled to the restriction 19 if the valve 13 is tight. After that, a first flow q1, for example of 10 µl/min, is produced and delivered to the first channel 11 of the liquid delivery system 1 with the flow source 5. The second channel 17 upstream of the valve 13 behaves like a pressure-tight chamber coupled to the according flow source 5; 45, 57. Subsequently, the second channel 17 is pressurized to a second pressure p2. Concurrently, the sensor readings of the flow rate sensor 9 within the delivery channel 11 are stored at least once while executing each of the features above or advantageously an average readings value for each of the features above is generated.

In embodiments, the flow source 5 is set to a flow of zero and the delivery channel 11 is depressurized before executing the method.

In other embodiments, the flow rate within the delivery channel is measured before and after the flow check valve opens induced by the flow q1 within the delivery channel 11.

In further embodiments, the flow rate within the delivery channel 11 is measured before and after the flow check valve 13 opens induced by the flow q1 within the delivery channel 11 while the second channel 17 is held at pressure p1 and while the second channel 17 is held at pressure p2.

The described leak check may be implemented as automated procedure as the user will not need to manipulate hydraulic pathways manually or use manual valves to check the systems tightness, instead the system may be used in the same configuration as for solvent delivery.

In other embodiments, the flow rate sensor 9 can be calibrated. The readings of the mass flow rate sensor 9 can depend strongly on the physical properties of the solvent, e.g. density, viscosity, thermal conductivity and specific heat. A flow rate sensor built into a liquid chromatography pump may be used with a variety of solvents, dilutions and mixtures, the characteristic sensor response curves of which are unknown. Firstly, a plurality of increasing flows q1 to qn is produced very precisely with the flow source 5. Concurrently, the sensor readings of the sensor 9 reflecting the flow rate in the delivery channel 11 are acquired after they have become stable at least once while each flow q1 to qn is set by the flow source 5. The pressure source 7 can be switched off while executing the calibrating process. Some flow rate sensors like the "Sensirion on-chip sensor" type have unique response characteristics for any individual sensor chip with any liquid. Therefore each chip must be calibrated for any desired solvent individually. In embodiments, the sensor output value is stored when it has become stable at the respective flow rate. A typical calibration run comprises flow rates from zero to 500 micro litres per minute depending on the sensor type and model.

Advantageously, the restriction 19 can be removed for calibrating the system 1 at low pressure values, for example at a pressure p3, in particular at a pressure of zero. Advantageously, the calibrating process can be executed after leakage checking the liquid delivery system 1 that ensures that the calibration measurement in the second part is taken in a leak proof hydraulic system 1 where the correct mass flow passes the sensor 9 during metering. In embodiments, it can be ensured in different way that the system is leak proof.

Possibly, the method as described above can be executed in single features respectively a plurality of single methods, for example as a method of leakage checking of the valve of the liquid delivery system 1, a method of leakage checking of the channel of the liquid delivery system 1, and/or a method of calibrating the flow rate sensor of the liquid delivery system, for example in this order.

The liquid delivery system can be adapted for supplying at least one microfluidic process, for example a liquid chromatographic process, for example a high pressure liquid chromatographic process. Therefore, the liquid delivery system can be coupled to an according microfluidic device and or to a laboratory apparatus. For example to a chromatographic system, a high performance fluid chromatographic system, an HPLC arrangement comprising a chip and an mass spectrograph, a high throughput LC/MS system, a purification system, micro fraction collection/spotting system, a system adapted for identifying proteins, a system comprising a GPC/SEC column, a nanoflow LC system, and/or a multidimensional LC system adapted for separation of protein digests, or alike.

For analyzing the liquid or rather one or more components within the liquid, the coupled microfluidic device can comprise a detection area, such as an optical detection area and/or an electrical detection area being arranged close to a flow path, for example being coupled to the channel of the liquid delivery system. Otherwise, the liquid delivery system can be part of a laboratory arrangement, for example comprising a mass spectrometer, for analyzing the liquid being delivered and/or transported by the liquid delivery system.

It is to be understood that embodiments of this invention are not limited to the particular component parts of the devices described or to process steps of the methods described as such devices and methods may vary. It is also to be understood, that the terminology used herein is for purposes describing particular embodiments only and it is not intended to be limiting. It must be noted that, as used in the specification and the appended claims, the singular forms of "a", "an", and "the" include plural referents until the context clearly dictates otherwise. Thus, for example, the reference to "a liquid delivery channel" or to a "first channel" includes two or more such functional elements.

What is claimed is:

1. A method of leakage checking of a valve of a liquid delivery system comprising at least one channel, having the valve and a flow sensing device, and a pressure source arranged downstream of the at least one channel and being capable of generating variable pressures, the method comprising:

pressurizing the at least one channel with the pressure source;

measuring a value of flow rate within the at least one channel with the flow sensing device; and comparing the measured value of flow rate for at least two different pressure values provided by the pressure source or to a known zero point value of the flow sensing device; and deriving an indication of leakage of the valve from the comparison of the measured flow rates.

2. The method of claim 1, comprising any one of the following:

the method further comprising setting a flow source to zero flow prior to pressurizing the at least one channel;

the method further comprising depressurizing the at least one channel prior to pressurizing the at least one channel;

wherein the measured value of flow rate for at least two different pressure values is obtained by measuring the flow rate within the at least one channel of the liquid delivery system with the flow sensing device, at least once while executing pressurization;

wherein the measured value of flow rate is obtained by using averaged, filtered, or otherwised processed readings of multiple measurements during execution of the method of claim 1;

wherein the measured value of flow rate is obtained by measuring the flow rate within the at least one channel with the flow sensing device at least once at the same flow rate setting of the flow source;

wherein the at least one channel comprises at least a first and second channel, and wherein pressurizing the at least one channel with the pressure source and measuring a value of flow rate within the at least one channel with the flow sensing device comprise:

pressurizing the second channel to a first pressure p1;

delivering a first flow q1 into the first channel with the flow source;

measuring the flow rate within the first channel with the flow rate sensors;

pressurizing the second channel to a second pressure p2; and measuring the flow rate within the first channel with the flow rate sensor.

3. The method of claim 1, comprising comparing the measured flow rate values before and after the valve opens accordingly.

* * * * *